(12) United States Patent
Millet Aguilar-Galindo et al.

(10) Patent No.: US 9,138,423 B2
(45) Date of Patent: Sep. 22, 2015

(54) USE OF INHIBITORS OF PORPHOBILINOGEN DEAMINASE IN THE TREATMENT OF CONGENITAL ERYTHROPOIETIC PORPHYRIA

(75) Inventors: Oscar Millet Aguilar-Galindo, Vizcaya (ES); Ana Laín Torre, Vizcaya (ES)

(73) Assignee: Asociación Centro de Investigación Cooperativa en Biociencias—CIC Biogune, Vizcaya (ES)

( * ) Notice: Subject to any disclaimer, the term of this patent is extended or adjusted under 35 U.S.C. 154(b) by 159 days.

(21) Appl. No.: 13/813,650

(22) PCT Filed: Aug. 5, 2011

(86) PCT No.: PCT/EP2011/063559
§ 371 (c)(1),
(2), (4) Date: Mar. 13, 2013

(87) PCT Pub. No.: WO2012/017088
PCT Pub. Date: Feb. 9, 2012

(65) Prior Publication Data
US 2013/0172397 A1    Jul. 4, 2013

(30) Foreign Application Priority Data

Aug. 5, 2010  (ES) .................................. 201031226

(51) Int. Cl.
*A61K 31/40* (2006.01)
*A61K 31/4025* (2006.01)
*A61K 31/404* (2006.01)
*A61K 31/405* (2006.01)

(52) U.S. Cl.
CPC .............. *A61K 31/40* (2013.01); *A61K 31/404* (2013.01); *A61K 31/405* (2013.01); *A61K 31/4025* (2013.01)

(58) Field of Classification Search
CPC . A61K 31/40; A61K 31/4025; A61K 31/404; A61K 31/405
USPC .................................. 514/415, 419, 422, 427
See application file for complete search history.

(56) References Cited

PUBLICATIONS

Frydman, Rosalia B et al., "The Enzymic inactivation of porphobilinogen deaminase", Biochimica et Biophysica Acta, 1973, 293, 2, pp. 506-513.

Guarini L et al., "Hydroxyurea in congenital erythropoietic porphyria", The New England Journal of Medicine, 1994, vol. 330, No. 15, pp. 1091-1092.
International Search and Written Opinion corresponding to International Patent Application No. PCT/EP2011/063559 dated Oct. 20, 2011.
Rank, J. M. et al., "Hematin therapy in late onset congenital erythropoietic porphyria", British Journal of Haematology, 1990, 75, 4, pp. 617-618.
Scott et al., "Concerning the catalytic site of porphobilinogen deaminase", Journal of the American Chemical Society, 1988, vol. 110, No. 17, pp. 5898-5900.
Yamauchi, K. et al., "Pyridoxal 5-phosphate therapy in a patient with myelodysplastic syndrome and adult onset congenital erythropoietic porphyria", British Journal of Haematology, 1992, 81, 4, pp. 614-615.

*Primary Examiner* — Shengjun Wang
*Assistant Examiner* — Jody Karol
(74) *Attorney, Agent, or Firm* — Jenkins, Wilson, Taylor & Hunt, P.A.

(57) ABSTRACT

The invention relates to the use of a compound of general formula (I), wherein $R^1$ and $R^2$ are independently H or $C_1$-$C_6$ alkyl, or $R^1$ and $R^2$ are bound to one another forming an optionally substituted fused benzene ring, $R^3$ is H, $C_1$-$C_6$ alkyl or —$CH_2$— $CH(NH_2)$—COOH and $R^4$ is H, $C_1$-$C_6$ alkyl, or $R^4$ represents (II) or (III) in the preparation of a medicinal product for treating and/or preventing congenital erythropoietic porphyria (CEP).

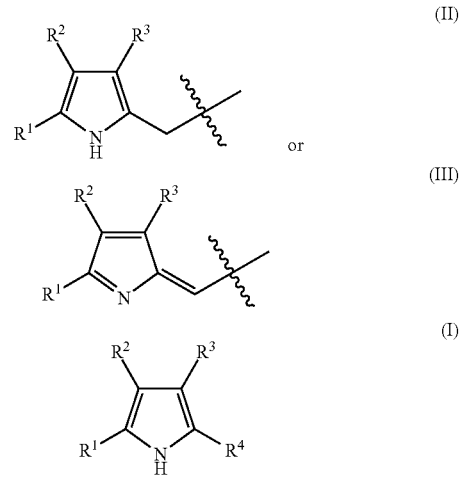

15 Claims, 2 Drawing Sheets

USE OF INHIBITORS OF PORPHOBILINOGEN DEAMINASE IN THE TREATMENT OF CONGENITAL ERYTHROPOIETIC PORPHYRIA

CROSS-REFERENCE TO RELATED APPLICATIONS

This application is filed under the provisions of 35 U.S.C. §371 and claims the priority of International Patent Application No. PCT/EP2011/063559 filed on Aug. 5, 2011, and of Spanish Patent Application No. P201031226 filed on Aug. 5, 2010. The disclosures of the foregoing international patent application and Spanish patent application are hereby incorporated by reference herein in their respective entireties.

FIELD OF THE INVENTION

The present invention relates to the use of compounds having inhibitory capacity to inhibit the catalytic activity of porphobilinogen deaminase in the treatment and/or prevention of congenital erythropoietic porphyria (CEP).

BACKGROUND OF THE INVENTION

The group of pathologies produced by a lack of activity in some of the enzymes of the heme group biosynthesis is generically known as porphyria. Normally the loss of activity is produced by mutations in the amino acid sequence of said proteins and the type of porphyria depends on the specific enzyme causing the mutation. The heme group biosynthesis is shown in scheme 1 indicating the enzymes involved in each stage of the pathway (above the reaction arrow) and detailing the names of the specific pathologies caused by functioning deficiencies in each of these enzymes (below the reaction arrow) [P=propionate, A=acetate, V=vinyl, M=methyl].

Scheme 1

Congenital erythropoietic porphyria (CEP) also known as Günther's disease named after the author who described it in 1911, is a hereditary disease and the least frequent of the porphyrias. This disease is a consequence of a malfunction in the uroporphyrinogen III synthase (UROIIIS), which is an enzyme of 260 residues (in the human isoform) catalyzing the cyclization of the linear tetrapyrrole hydroxymethylbilane to produce macrocycle uroporphyrinogen III (or urogen III), the precursor of the heme groups, siroheme, $F_{340}$, vitamin $B_{12}$ and chlorophyll. The tetrapyrrole substrate is highly unstable and in the absence of the UROIIIS enzyme it spontaneously degrades to uroporphyrinogen I (uroporphyrinogen I and III differ only in the position of a P group and an A group in the D ring of the cycle). The cyclization of the preuroporphyrinogen for producing uroporphyrinogen III (enzymatic pathway) or uroporphyrinogen I (spontaneous degradation) is shown in scheme 2.

Scheme 2

Uroporphyrinogen I and its derivatives are difficult to catabolize byproducts that tend to accumulate in the body. Thus, large amounts of uroporphyrinogen I which accumulate in bags below the eyes and deform the extremities are produced in CEP patients (those having a UROIIIS deficiency). Depending on its severity, other common symptoms of the disease are, for example, an extreme sensitivity to sunlight from infancy that manifests as intense dermal lesions in the exposed areas, bone and cartilage destruction, erythrodontia (dark brown coloration of the teeth, especially baby teeth due to the porphyrin accumulation), anemia, etc.

Today, the only curative treatment for CEP is a bone marrow transplant, i.e., replacing the bone marrow of the CEP patient (recipient) with the healthy bone marrow of another person (donor). After an effective transplant the clinical characteristics of CEP, such as photosensitivity or anemia are resolved. However, the scars from previous skin lesions are permanent. Furthermore, for a successful transplant the bone marrow of the donor must have high similarity to that of the recipient. In this sense, the bone marrow transplant is a high-risk treatment and powerful treatments inhibiting the recipient's immune system are initially required to prevent rejection. Due to all of this, a bone marrow transplant is reserved for those severely affected individuals having an identical bone marrow donor.

Therefore to this day, the treatment of CEP is only limited to attempting to prevent or relieve its symptoms, such as for example, by using sunscreens to prevent skin and eye scars, the continuous administration of heme derivatives or transfusing blood to counteract heme group deficiency, etc.

Although the inhibition of porphobilinogen deaminase (PBGD; the enzyme also known as hydroxymethylbilane synthase or uroporphyrinogen I synthase) would imply the reduction of the amount of preuroporphyrinogen and therefore an improvement of life conditions for CEP patients, all the studies performed in this sense up until now have been unfavorable. The PBGD enzyme has been subjected to an intense mechanistic study [Louie G V et. al. (1992) Nature 359: 33-39; Jordan P M, Woodcock S C (1991) The Biochemical journal 280 (Pt 2): 445-449]. The identification of the substrate binding site has involved the development of "suicidal" inhibitors (that covalently bind to the enzyme and prevent the progression of the reaction). It particularly relates to derivatives of the enzymatic substrate such as 2-bromoporphobilinogen [Battersby A R (2000) Natural product reports 17: 507-526; Jones R M, Jordan P M (1994) The Biochemical journal 299 (Pt 3): 895-902; Warren M J, Jordan P M (1988) Biochemistry 27: 9020-9030] or 6-methylporphobilinogen and 6,11-ethanoporphobilinogen [Ahmed R, Leeper F J (2003) Org Biomol Chem 1: 21-23]. It has also been found that porphyrins can inhibit enzyme [Araujo L S et. al. (1994) Int J Biochem 26: 1377-1381]. Despite their specificity, their efficiency as in vivo inhibitors has not been demonstrated, and their high reactivity rules them out as potential drugs. In fact, it would be expected that these porphobilinogen derivatives generate many problems in vivo as they bind covalently to the enzyme and permanently inactivating it. Furthermore, the substrate is a secondary metabolite and therefore analogous inhibitors thereof could have inhibitory activity on other enzymes reducing the in vivo selectivity.

Given that there is a cysteine involved in the catalysis mechanism, PBGD protein modifying agents have also been studied. It has been found that some substances such as metal ions or 2-mercaptoethanol can significantly alter the catalytic activity of the porphobilinogen deaminase of Arabidopsis thaliana [Jones R M, Jordan P M (1994) The Biochemical journal 299 (Pt 3): 895-902]. However, this is due to a non-specific chemical modification mechanism of the enzyme and not due to a specific binding of the molecule in the active site of the protein. Likewise, the studied model is being questioned since a low inhibition by N-ethylmaleimide is seen, while the same reactant strongly deactivates the *Escherichia coli* enzyme [Warren M J, Jordan P M (1988) *Biochemistry* 27: 9020-9030]. The complete list of tested substances can be found in the database Brenda: http://www.brenda-enzymes.org/php/result_flat.php4?ecno=2.5.1.61

In view of aforementioned, there is still a need of providing therapeutic agents with inhibitory capacity to inhibit the catalytic activity of porphobilinogen deaminase potentially useful in the prevention and/or treatment of congenital erythropoietic porphyria (CEP). In addition to being effective, said compound inhibitors advantageously should not cause undesirable toxicity. Likewise, from their synthesis point of view and pharmacological screening point of view, it would be highly desirable that the compounds can be easily modulated.

SUMMARY OF THE INVENTION

The present invention addresses the problem of providing new therapeutic agents for the treatment and/or prevention of congenital erythropoietic porphyria (CEP).

The authors of the present invention have surprisingly found a new line of inhibitors that inhibit the catalytic activity of the porphobilinogen deaminase which are not analogous to the substrate and which provide a reversible inhibition. Advantageously, these compounds have an "inhibiting" part, a main part responsible for the activity, and a "modular" part, the structural modification of which would allow improving the pharmacological properties of the compound without significantly altering the inhibitory capacity of same. Furthermore, since some of these compounds are natural metabolites or are very similar (chemically) with natural metabolites, it is expected that the toxicity of the compounds is low. This fact is especially important in the case of rare diseases such as in the case of CEP since the lack of patients limits or makes the development of the clinical phases of the medicinal product impossible.

Therefore, in one aspect, the invention relates to the use of a compound of general formula (I) (compounds of the invention) wherein (I)

$R^1$ and $R^2$ are independently selected from the group consisting of H and $C_1$-$C_6$ alkyl, or $R^1$ and $R^2$ are bound to one another forming an optionally substituted fused benzene ring, $R^3$ is selected from the group consisting of H, $C_1$-$C_6$ alkyl and $R^4$ is selected from the group consisting of H and $C_1$-$C_6$ alkyl, or $R^4$ represents in the preparation of a medicinal product for treating and/or preventing congenital erythropoietic porphyria (CEP).

In another aspect, the invention relates to the compound of general formula (I) previously defined for its use in the treatment and/or prevention of congenital erythropoietic porphyria (CEP).

In an additional aspect, the invention relates to a method for the prevention and/or treatment of congenital erythropoietic porphyria (CEP) in a subject comprising the administration of a therapeutically effective amount of a compound of formula (I) to said subject. In a preferred embodiment, said subject is a human being.

DETAILED DESCRIPTION OF THE INVENTION

For the purpose of facilitating the understanding of the present invention, the meaning of some terms and expressions as used in the context of the invention are included in this document below.

"Alkyl" refers to a saturated linear or branched hydrocarbon chain radical consisting of carbon and hydrogen atoms which is bonded to the rest of the molecule by means of a single bond. When "$C_1$-$C_6$ alkyl" is indicated, it refers to a alkyl group of one, two, three, four, five or six carbon atoms such as for example, methyl, ethyl, propyl, isopropyl or n-butyl. In certain embodiments of the present invention, the alkyl group is particularly methyl.

"Halide" or "halogen" means —F, —Cl, —Br or —I. In certain embodiments of the present invention, the halide group is particularly fluorine.

The authors of the present invention have demonstrated that the compounds of general formula (I) inhibit the activity of the porphobilinogen deaminase (PBGD) such that less amount of preuroporphyrinogen is produced, and therefore, the accumulation of uroporphyrinogen I derived from a malfunction of UROIIIS in congenital erythropoietic porphyria (CEP) patients is reduced.

One of the advantages associated with the compounds of formula (I) is that they made up a family of inhibitors that can be easily modulated, a very important feature for pharmaceutical development. Also, unlike the porphobilinogen derivatives studied in the state of the art as inhibitors of PBGD, the compounds of the invention compete with the substrate to bind non-covalently to the active site of the protein (reversible inhibition). The porphobilinogen is also a secondary metabolite and therefore the problems of in vivo selectivity that could produce inhibitors similar to the substrate are prevented.

In a preferred embodiment of the invention, $R^4$ and $R^2$ in the compound of general formula (I) are independently selected from the group consisting of H and methyl, or $R^1$ and $R^2$ are bound to one another forming a fused benzene ring unsubstituted or substituted in position 4 or 7 of the indole with methyl or halogen (preferably fluorine).

Furthermore, preferred compounds of formula (I) are those wherein at least two of $R^1$, $R^2$, $R^3$ and $R^4$ simultaneously represent methyl.

In another preferred embodiment of the invention, $R^3$ in the compound of general formula (I) is selected from the group consisting of H, methyl and In another preferred embodiment of the invention, $R^4$ in the compound of general formula (I) is selected from the group consisting of H and methyl, or $R^4$ represents In additional preferred embodiments, the previously described preferences for the different substituents are combined. The present invention also refers to such combinations of preferred substitutions in the previous formula (I).

Particularly preferred compounds of the invention are listed in the following table:

| Name of the compound | Acronym |
|---|---|
| 2S-amino-3-(1H-indol-3-yl) propanoic acid (L-Tryptophan) | LTRP |
| 2R-amino-3-(1H-indol-3-yl) propanoic acid (D-Tryptophan) | DTRP |
| 2,3-benzopyrrole (indole) | IND |
| pyrrole | PYR |
| 2S-amino-3-(1H-indol-7-fluoro-3-yl) propanoic acid | 7F-TRP |
| 2R-amino-3-(1H-indol-7-methyl-3-yl) propanoic acid | CH3-TRP |
| 3,5,3',5'-tetramethyl-1H, 2'H-2, 2'-methylylidene-bis-pyrrole | bis-PYR |
| 2-(1H-pyrrol-2-ylmethyl)-1H-pyrrole | di-PYR |
| 2,4-dimethyl-1H-pyrrole | 2,4-CH3-PYR |
| 2,5-dimethyl-1H-pyrrole | 2,5-CH3-PYR |
| 2S-amino-3-(1H-indol-4-fluoro-3-yl) propanoic acid | 4F-TRP |

The chemical structure of the aforementioned compounds is included below:

The person skilled in the art will appreciate that the tryptophan derivatives have a chiral centre. The present invention also includes the racemic and enantiomer compounds of the aforementioned tryptophan derivatives.

As it has been previously indicated, the use of the compounds of general formula (I) in the treatment and/or prevention of congenital erythropoietic porphyria (CEP) relates to its capacity for inhibiting the catalytic activity of the porphobilinogen deaminase (PBGD) enzyme, preferably human PBGD.

For the person skilled in the art, the compounds of formula (I) are easily accessible either commercially or by means of conventional synthesis methods from commercial or widely known compounds or intermediates. In this sense, many companies market a large variety of pyrrole, indole and the amino acid tryptophan derivatives as well as compounds of formula (I) consisting two pyrrole rings. On the other hand, synthetic processes for preparing the compounds of the invention can be consulted in general organic chemistry (see for example, March's Advanced Organic Chemistry Reactions, Mechanisms, and Structure; Wiley-Interscience, $5^a$ Ed.) or heterocyclic chemistry references. Additionally, documents related with porphyrin synthesis disclose different methods for preparing dipyrromethanes and dipyrromethenes (see for example, Karl M. Kadish, Kevin M. Smith, Roger Guilard, The Porphyrin Handbook: Synthesis and organic chemistry; Academic Press, 1999).

In a particular embodiment, the compound of formula (I) will be formulated in a pharmaceutically suitable composition in a therapeutically effective amount together with one or more pharmaceutically acceptable carriers, adjuvants or excipients for its administration in the prevention and/or treatment of congenital erythropoietic porphyria (CEP).

The term "carrier, adjuvant and/or excipient" refers to molecular entities or substances with which the active ingredient is administered. Such pharmaceutical carriers, adjuvants or excipients can be sterile liquids such as water and oils, including those from petroleum or animal, plant or synthetic origin, such as peanut oil, soybean oil, mineral oil, sesame oil and the like, excipients, disaggregates, humectants, diluents, etc. Suitable pharmaceutical carriers are described in "Remington's Pharmaceutical Sciences" by E. W. Martin.

The pharmaceutical compositions can be administered by any suitable administration route, for example, oral route, parenteral route (for example, subcutaneous route, intraperitoneal route, intravenous route, intramuscular route, etc.), etc., preferably by oral route.

In a particular embodiment, said pharmaceutical compositions can be in a pharmaceutical dosage form administered by oral route either in solid or liquid form. Illustrative examples of pharmaceutical dosage forms administered by oral route include tablets, capsules, granules, solutions, suspensions, etc., and they can contain conventional excipients such as binders, diluents, disintegrating agents, lubricants, humectants, etc., and they can be prepared by conventional methods. The pharmaceutical compositions also can be adapted for their parenteral administration in the form of, for example, sterile solutions, suspensions or lyophilized products in the suitable dosage form; in this case, said pharmaceutical compositions will include the suitable excipients such as buffers, surfactants, etc. In any case, the excipients will be chosen depending on the selected pharmaceutical dosage form. A review of the different pharmaceutical dosage forms of drugs and of their preparation can be found in the book "Tratado de Farmacia Galénica", by C. Faulí i Trillo, 10 Edition, 1993, Luzán 5, S. A. de Ediciones.

For its application the compound of formula (I) will preferable be in an acceptable or substantially pure form, i.e., having a pharmaceutically acceptable purity level excluding the pharmaceutically acceptable excipients and not including material considered to be toxic at normal dosage levels. The levels of purity for the compound of formula (I) are preferably greater than 50%, more preferably greater than 70%, more preferably greater than 90%. In a preferred embodiment, they are greater than 95%.

As it is used herein, the expression "therapeutically effective amount" refers to the amount of active component (compound of formula (I)) calculated for producing the desired effect and will generally be determined by, among other causes, the characteristics of the compound of formula (I) themselves and the therapeutic effect to be achieved. It will also depend on the subject to be treated, the severity of the disease suffered by said subject, the chosen dosage form, etc. For this reason, the doses mentioned in this invention must be considered only as guides for the person skilled in the art, and he must adjust the doses depending on the aforementioned variables. However, the compound of formula (I) can be administered one or more times a day, for example, 1, 2, 3 or 4 times a day in a typical total daily amount comprised between 1 and 10 mg/kg of body mass/day, preferably 1 mg/kg of body mass/day.

By principle, although the pharmaceutical composition provided by this invention can be used for treating any subject, in a particular embodiment, the pharmaceutical composition of the invention is especially useful in humans as it inhibits the catalytic activity of the human porphobilinogen deaminase enzyme.

The compound of formula (I) as well as the pharmaceutical compositions containing them can be used together with other additional useful drugs in the prevention and/or treatment of congenital erythropoietic porphyria. Said additional drugs can form part of the same pharmaceutical composition or, alternatively, can be provided in the form of a separated composition for their simultaneous or sequential administration to that of the pharmaceutical composition comprising the compound of formula (I). For example, the treatment with a compound of formula (I) could be complimented with the administration of heme derivatives or blood products to counteract the heme group deficiency.

The invention is illustrated below by means of the following examples that must to be considered as merely illustrative and not limiting the scope of the invention.

EXAMPLES

Materials and Methods

Obtaining and purifying the enzyme: The enzyme is obtained and purified by following the method published by Millet O et al. (2009) *Biochemistry* 48: 454-461.

Enzymatic assay: The assay is based on the method described by Jordan (Shoolingin-Jordan P M et al. (1997). *Methods in enzymology* 281: 327-336) with some modifications. 10 μL of porphobilinogen deaminase (PBGD) at a concentration of 150 μM in 48 μL of buffer (20 mM Tris-HCl pH 8.0, NaCl 150 mM) is preheated at 37° C. for two minutes. If the assay is performed in the presence of an inhibitor, the latter is added in dissolved form into the buffer. 25 μL of the porphobilinogen (PBG) substrate are then added, diluted to different concentrations (0.15, 0.3, 0.45, 0.6, 0.9, 1.2, 1.5, 1.8, 2.1, 2.4, 2.7, 3, 3.3, 3.9 mM) in the aforementioned buffer and are incubated at 37° C. for five minutes. A control assay containing a buffer without substrate (PBG) in the same proportions is performed at the same time. The enzymatic reaction is stopped by means of freezing the samples in liquid nitrogen. Then the mixture is incubated again with 6 μL of 25 mM uroporphyrinogen 3 synthase (U3S) at 37° C. for 30 minutes to transform the pre-uroporphyrinogen into uroporphyrinogen III. The reaction is again stopped by means of freezing in liquid nitrogen. Then the formed $CO_2$ and uroporphyrinogens are oxidized to uroporphyrins by means of adding 25 μL of I2/KI solution and incubation for 10 minutes in ice and darkness. The iodine excess is then bleached by adding 25 μL of saturated sodium metabisulfite solution. 250 μL of 10% trichloroacetic acid (TCA) are added to precipitate the protein and the samples are centrifuged at 13,000 r.p.m. for 5 minutes. Finally, different dilutions of the supernatant in 0.1 M HCl are prepared to measure the change of absorbance at 405 nm with respect to the control sample.

Calculation of inhibition constants: Inhibition constants have been calculated from the global data fitting of all values in presence of inhibitor according to the methodologies disclosed in the prior art (Structure and mechanism in protein Science, Alan Fersht, 1999, Ed. Freeman and Co. (New York), Pag. 105-115).

Example 1

Figure 1:
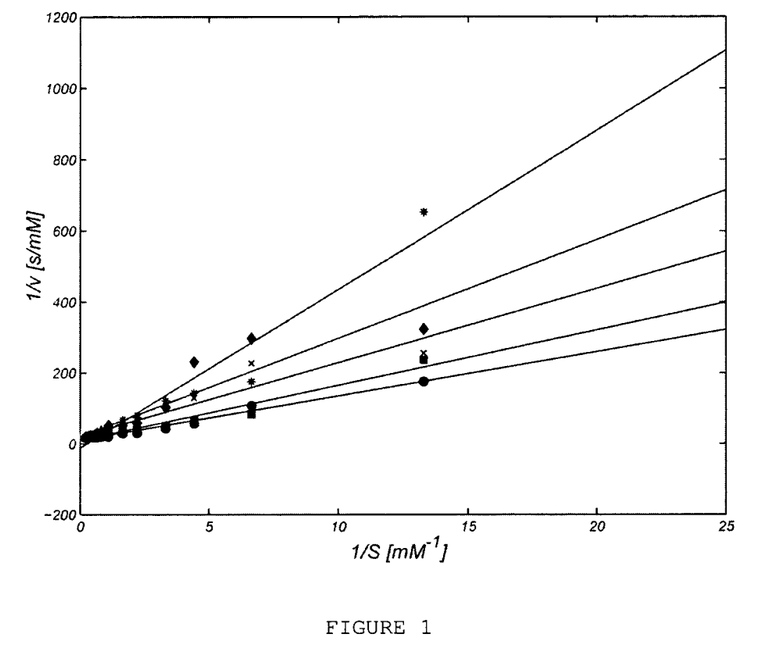
FIG. 1 shows the Lineweaver-Burk (LwB) plot for PBGD in the absence (●) and in the presence of an increasing amounts of 7-fluoro-tryptophan (F-TRP): 1 mM (■), 5 mM (x), 8.5 mM (♦) and 10 mM (*). The symbols correspond to the experimentally determined values meanwhile the lines show the linear regressions thereof.

Evaluation of the Effect of 7-Fluoro-Tryptophan Inhibitor on Porphobilinogen Deaminase Increasing amounts of 7-fluoro-tryptophan (F-TRP) show a progressive inhibition of the catalytic activity following a competitive inhibition scheme (Fersht A. (1999) Structure and mechanism in protein science. A guide to enzyme catalysis and protein folding. Ed. Freeman and Co. New York.) wherein the inhibitor and the substrate compete to bind non-covalently to the active site of the protein. The Lineweaver-Burk (LwB) plot depicted in FIG. 1 shows the results obtained. The change in slope but with the same intercept in a LwB plot is indicative of a competitive inhibition.

Example 2

Evaluation of the Effect of Indole Inhibitor on Porphobilinogen Deaminase

Figure 2:
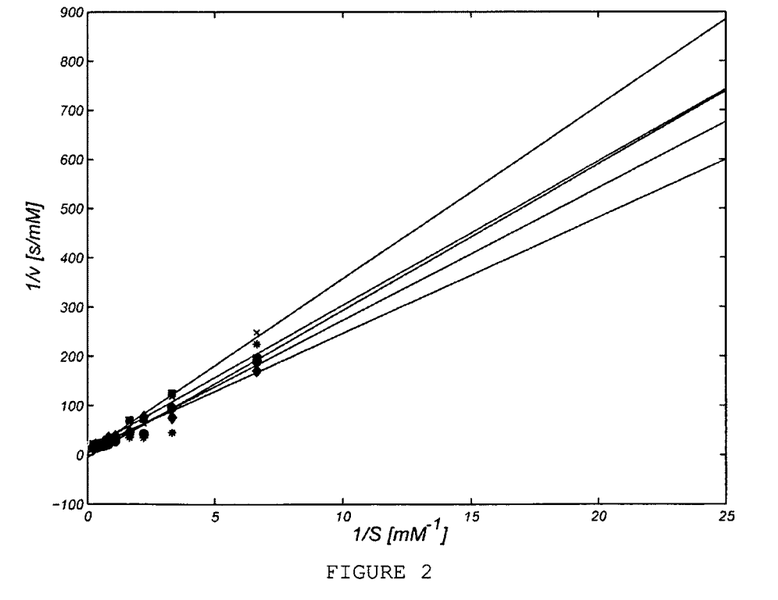
FIG. 2 shows the Lineweaver-Burk (LwB) plot for PBGD in the absence (●) and in the presence of an increasing amounts of indole (IND): 500 µM (■), 1 mM (x), 2 mM (♦) and 5 mM (*). The symbols correspond to the experimentally determined values meanwhile the lines show the linear regressions thereof.

Indole (IND) also shows the capacity for inhibiting the catalytic activity of PBGD following a competitive inhibition scheme wherein the inhibitor and the substrate compete to bind non-covalently to the active site of the protein. The Lineweaver-Burk (LwB) plot depicted in FIG. 2 shows the results obtained. The change in slope but with the same intercept in a LwB plot is indicative of a competitive inhibition.

Example 3

Evaluation of the Effect of D-Tryptophan Inhibitor on Porphobilinogen Deaminase

Figure 3:
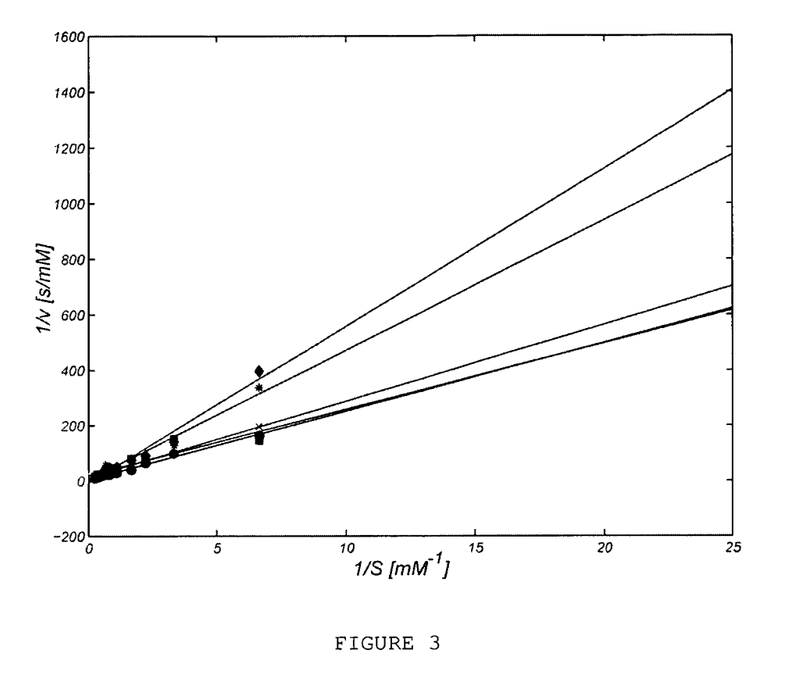
FIG. 3 shows the Lineweaver-Burk (LwB) plot for PBGD in the absence (●) and in the presence of an increasing amounts of D-tryptophan (DTRP): 1 mM (■), 1.5 mM (x), 2.5 mM (♦) and 5 mM (*). The symbols correspond to the experimentally determined values meanwhile the lines show the linear regressions thereof.

D-tryptophan (DTRP) also shows capacity for inhibiting the catalytic activity of PBGD following a competitive inhibition scheme wherein the inhibitor and the substrate compete to bind non-covalently to the active site of the protein. The Lineweaver-Burk (LwB) plot depicted in FIG. 3 shows the results obtained. The change in slope but with the same intercept in a LwB plot is indicative of a competitive inhibition.

Example 4

Evaluation of the Effect of Pyrrole Inhibitor on Porphobilinogen Deaminase

Figure 4:
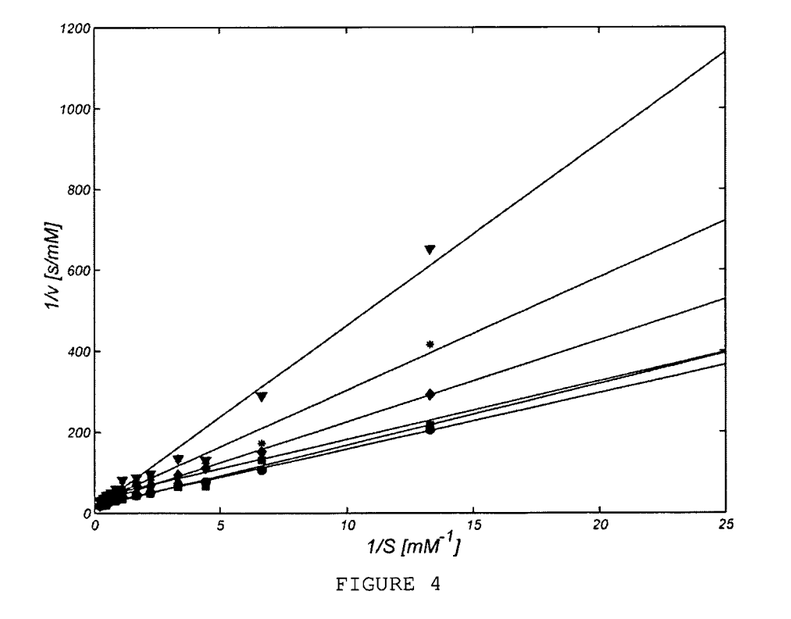
FIG. 4 shows the Lineweaver-Burk (LwB) plot for PBGD in the absence (●) and in the presence of an increasing amounts of pyrrole (PYR): 2.5 mM (■), 5 mM (x), 7.5 mM (♦), 10 mM (*) and 15 mM (▼). The symbols correspond to the experimentally determined values meanwhile the lines show the linear regressions thereof.

Pyrrole (PYR) also shows capacity for inhibiting the catalytic activity of PBGD following a competitive inhibition scheme wherein the inhibitor and the substrate compete to bind non-covalently to the active site of the protein. The Lineweaver-Burk (LwB) plot depicted in FIG. 4 shows the results obtained. The change in slope but with the same intercept in a LwB plot is indicative of a competitive inhibition.

Example 5

Inhibition Constants on Porphobilinogen Deaminase

The following table shows the inhibition constants (Ki) of the catalytic activity of the PBGD for some compounds of the invention:

| Name of the compound | Acronym | Ki |
| --- | --- | --- |
| 2,4-dimethyl-1H-pyrrole | 2,4-CH3-PYR | 6 μM |
| 2,5-dimethyl-1H-pyrrole | 2,5-CH3-PYR | 3 μM |

The invention claimed is:

1. A method for the treatment of congenital erythropoietic porphyria (CEP) in a subject in need thereof comprising the administration to said subject of a therapeutically effective amount of a compound of formula (I)

wherein
$R^1$ and $R^2$ are independently selected from the group consisting of H and $C_1$-$C_6$ alkyl, or $R^1$ and $R^2$ are bound to one another forming an optionally substituted fused benzene ring,
$R^3$ is selected from the group consisting of H, $C_1$-$C_6$ alkyl and

$R^4$ is selected from the group consisting of H and $C_1$-$C_6$ alkyl, or $R^4$ represents

2. The method according to claim 1, wherein, in the compound of formula (I), $R^1$ and $R^2$ are independently selected from the group consisting of H and methyl, or $R^1$ and $R^2$ are bound to one another forming a fused benzene ring that is unsubstituted or substituted in position 4 or 7 of the indole with methyl or halogen.

3. The method according to claim 1, wherein, in the compound of formula (I), at least two of $R^1$, $R^2$, $R^3$ and $R^4$ simultaneously represent methyl.

4. The method according to claim 1, wherein in the compound of formula (I), $R^3$ is selected from the group consisting of H, methyl and

5. The method according to claim 1, wherein in the compound of formula (I), $R^4$ is selected from the group consisting of H and methyl, or $R^4$ represents

6. The method according to claim 1, wherein the compound of formula (I) is selected from the group consisting of:

7. The method according to claim 1, wherein the compound of formula (I) inhibits catalytic activity of the porphobilinogen deaminase (PBGD) enzyme.

8. The method according to claim 2, wherein in the compound of formula (I), $R^3$ is selected from the group consisting of H, methyl and

9. The method according to claim 3, wherein in the compound of formula (I), $R^3$ is selected from the group consisting of H, methyl and

10. The method according to claim 2, wherein in the compound of formula (I), $R^4$ is selected from the group consisting of H and methyl, or $R^4$ represents

11. The method according to claim 3, wherein in the compound of formula (I) $R^4$ is selected from the group consisting of H and methyl, or $R^4$ represents

12. The method according to claim 4, wherein in the compound of formula (I) $R^4$ is selected from the group consisting of H and methyl, or $R^4$ represents

13. The method according to claim 5, wherein in the compound of formula (I) R⁴ is selected from the group consisting of H and methyl, or R⁴ represents

15. The method according to claim 9, wherein in the compound of formula (I) R⁴ is selected from the group consisting of H and methyl, or R⁴ represents

14. The method according to claim 8, wherein in the compound of formula (I) R⁴ is selected from the group consisting of H and methyl, or R⁴ represents

\* \* \* \* \*